United States Patent [19]

Ishii et al.

[11] Patent Number: 5,186,944

[45] Date of Patent: Feb. 16, 1993

[54] THERAPEUTIC MEDICAMENT FOR THROMBOSIS

[75] Inventors: Yoichi Ishii; Hisashi Mihara, both of Miyazaki, Japan; Lee M. Ho, Seoul, Rep. of Korea; Goro Kimura, Kamakura, Japan

[73] Assignee: Eimei Company Ltd., Miyazaki, Japan

[21] Appl. No.: 807,406

[22] Filed: Dec. 12, 1991

Related U.S. Application Data

[63] Continuation of Ser. No. 475,021, Feb. 5, 1990, abandoned.

[30] Foreign Application Priority Data

Feb. 15, 1989 [JP] Japan .................................... 1-33701
Apr. 28, 1989 [JP] Japan .................................. 1-107250

[51] Int. Cl.⁵ .............................................. A61K 35/36
[52] U.S. Cl. ................................ 424/520; 424/94.64; 514/2; 514/21; 514/866; 530/855
[58] Field of Search .............. 424/520, 94.64; 514/2, 514/21, 866; 530/855

[56] References Cited

U.S. PATENT DOCUMENTS 4,568,545 2/1986 Mihara et al. ..................... 435/212
5,024,844 6/1991 Ishii et al. ............................ 424/520

FOREIGN PATENT DOCUMENTS 58-126770 7/1983 Japan .
59-216572 12/1984 Japan .
2116565 9/1983 United Kingdom .

Primary Examiner—David M. Naff
Assistant Examiner—Jean C. Witz
Attorney, Agent, or Firm—Wyatt, Gerber, Burke and Badie

[57] ABSTRACT

An efficient therapeutic medicament in a powdery form for thrombosis and related diseases is prepared by the steps of: removing dirty matters on the body surface and fecal mud in the digestive tracts from live earthworms by keeping them in a slightly acidified water bath at a specified temperature; mashing the cleaned earthworms into a mushy paste; and vacuum-drying the mushy paste of the earthworms by the stepwise temperature elevation up to 70° to 80° C. The results of the clinical tests of the medicament are presented.

3 Claims, No Drawings

THERAPEUTIC MEDICAMENT FOR THROMBOSIS

This application is a continuation of copending application Ser. No. 07/475,021, filed Feb. 5, 1990, abandoned.

BACKGROUND OF THE INVENTION

The present invention relates to a medicament useful for medical treatment of human diseases such as thrombotic diseases including lipemia, hypertension and hypotonia which originate in thrombus formation and complications with the thrombotic diseases, and also to a method for the preparation thereof using earthworms as the raw material.

Thrombi are continuously formed in human body but successively dissolved away by the fibrinolytically active enzymes occurring in human body. An imbalance between formation and disappearance of thrombi causes accumulation of unnecessary thrombi resulting in various diseases originating in thrombi. It is a serious problem in recent years that prime and aged persons frequently suffer from various diseases caused by thrombus accumulation such as transient cerebral ischemic attack, cerebral infarction, i.e. cerebral thrombosis or cerebral embolism, ischemic stenocardia, myocardial infarction, arterio-thrombosis, venous thrombo-sis, deep-venous thrombosis, peripheral arterio-obturation, peripheral venous obturation, pulmonary thrombosis, pulmonary embolism and the like.

Therefore, various pharmaceuticals have been developed as a medicament for these diseases among which medicament preparations from a thrombus-resolvent enzyme such as urokinase, streptokinase and the like are effective. Urokinase is particularly highlighted because of the excellent pharmacological activity thereof.

Urokinase is a kind of plasminogen-activators contained in human urine or cultured fetal renal cells and exhibits an effect of thrombus-resolvent by converting plasminogen into plasmin as a fibrinolytic enzyme. However, the direct activation of plasminogen by urokinase is simultaneously accompanied by the side effects of hemorrhage or decrease in the activated partial thromboplastin time due to the decrease of fibrin. Moreover, urokinase has a defect in administration that the patient unavoidably suffers a great pain since urokinase must be administered by instillation taking 1 to 12 hours in the form of a solution prepared by dissolving, for example, 60,000 to 1,000,000 units of the same in 500 to 1,000 ml of a physiological salt solution or 5% aqueous glucose solution.

On the other hand, streptokinase is produced by the culture of $\beta$-hemolytic streptococci and has an activity to indirectly activate plasminogen concurrently with reduction of fibrinogen. Nevertheless, streptokinase has several disadvantages that side effects, such as pyrexia, nausea, headache, convulsion, urticaria, hemorrhage and the like, are caused and, though in rare cases, hypotomia and anaphylaxis are caused, it has an antigenicity and is only poorly effective in the antibody-producing cases and it must be administered by the intravenous instillation like the aforementioned urokinase.

Apart from the above mentioned situation, earthworms as raw or as dried are known from old times as a kind of Chinese traditional medicines to have various pharmacological activities such as antipyretic, analgesic, diuretic and antidotal effects (see. for example, Tennen Yakubutsu Jiten, page 215, published Apr. 15, 1986, by Hirokawa Publishing Co.).

In recent years, proposals have been made for the use of the extracted effective constituents of earthworms as the thrombus-resolvent prepared by collecting specific fractions obtained in the chromatographic fractionation of the extract solution (see Japanese Patent Kokai 58-14S824, 59-63184 and 59-18413). However, such a product is not practical because the preparation procedure thereof involves very complicated and lengthy treatments of multiple steps in addition to the generally low yield of the product.

Also, the effectiveness of a freeze-dried powder of earthworms for medication of a patient of thrombosis is yet unknown notwithstanding the reported increase in the fibrin-degradation product supposedly derived from dissolved fibrin lumps in the blood of two among six normal persons orally administrated with the powder [Study Reports on Environmental Science B304 - R30, Reports of Specila Research Project of Environmental Science, Part 4, pages 107 to 112, 1986]. Moreover, freeze-dried powders of earthworms must be stored in a cold place of 0° C. or below or with addition of an antiseptic since removal of sundry germs therefrom is always incomplete and still have a problem of denaturation after a long-term storage Acta Haematologica Japonica, volume 45, page 503 (1982)].

SUMMARY OF THE INVENTION

In view of the above described present status of medicaments for thrombosis, the inventors have conducted extensive studies with an object to provide a medicament for thrombosis and a method for the preparation of the same using living bodies of earthworms. The inventive medicament for thrombosis exhibits a high therapeutic effect without the danger of any side effects. The inventive method for the preparation of the medicament is highly efficient and is suitable as an industrial process.

Namely, the present invention provides a medicament for thrombosis which comprises, as an effective ingredient, a powder prepared by subjecting a mashed living body of an earthworm freed from a dirty matter on the body surface and in the digestive tract thereof to vacuum-drying under such a condition that the temperature reaches 70° to 80° C. at the final stage. Removal of the dirty matter or fecal mud from the digestive tract of living earthworms is carried out by dipping and keeping living earthworms in water preferably having a pH of 3 to 6.5 controlled by adding an acid and kept at a temperature of 6° to 26° C. Vacuum drying is carried out by increasing the temperature stepwise.

DETAILED DESCRIPTION OF THE PREFERRED EMBODIMENTS

The inventors have conducted investigations with an object to provide a medicament for thrombosis not accompanied by any side effects preferably having storability for a long period in a stabilized condition by overcoming the defects of the prior art medicaments for thrombosis and using raw materials available at low costs.

The inventors have carried out extensive studies on the relationship between the tissues of earthworms and the pharmacological activity thereof and consequently arrived at a discovery that an active ingredient effective for medication of thrombosis is contained in a large amount in smooth muscular layers, body cavity fluids, blood, vascular tracts, abdominal neurofibrils, digestive tracts or intestines and digestive fluids while an inhibitor against the above mentioned active substance is contained in skin-mucous substances, skin and circular muscle layers and that the inhibitor and the hemolytic activity can be deactivated without decreasing the effectiveness as the medicament for thrombosis when undivided tissues of earthworms are converted into a powder under specific conditions thus to complete the present invention on the basis of the above mentioned discovery.

Thus, the present invention provides a medicament for thrombosis which comprises, as an effective ingredient, a powder obtained from a living body of earthworm freed from dirty matters on the body surface and in the digestive tracts by mashing and vacuum-drying under such conditions that the temperature is increased stepwise up to 70° to 80° C. at the final stage.

The earthworms used as the raw material in the preparation of the inventive medicament for thrombosis can be either those living in natural fields or those obtained by culturing. Earthworms of any species can be used without particular limitations including *Lumbricus rebellus* (Hoffmeister), *Lumbricus terrestris* (Linnaeus), *Eisenia foetida* (Savigny), *Allolobophora caliginosa* (Savigny), *Dendrobaena octaedra* (Savigny), *Allolobophora japonica* (Michaelsen), *Helodrilus foetidus* and the like belonging to the family of *Lumbricidae*; *Drawida hattamimizu* (Hatai) and the like belonging to the family of *Moniligastridae*; *Pheretima divergens* (Michaelsen), *Pheretima communissima* (Goto & Hacai), *Pheretima agrestis* (Goto & Hatai), *Pheretima sieboldi* (Horst), *Pheretima hilgendovfi* (Michaelsen), *Pontodrilus matsushimensis* (Iizuka) and the like belonging to the family of *Megascolecidae*; and *Criodrilus bathybates* and the like belonging to the family of *Glossoscolesidae*, of which particularly preferred are those belonging to the families of *Lumbricidae* and *Megascolecidae*. Earthworms of the family of *Lumbricidae* are more preferable because they are suitable for culturing.

Each body of these earthworms is constituted of a cylindrical body wall composed of a large number of interconnected ringform segments called metameres and has circular grooves called intermetamere grooves each interposed between two contiguous metameres. The body wall is composed of three layers of which the outermost layer is a skin, the intermediate is a muscular layer or a circular muscle layer and the innermost layer is a muscular layer with orientation in the longitudinal direction called a smooth muscular layer. Digestive tracts are found inside the body wall while the space between the body wall and the digestive tracts is filled with a viscous yellow or milky-white body cavity fluid. Other useful tissues include vascular tracts, abdominal neurofibrils, septums and the like, and the body fluids include blood, digestive fluids, skin-mucous sub stances and the like in addition to the body cavity fluid. Among these tissues and fluids, the active substance effective in medication of thrombosis is contained largely in the smooth muscular layers, body cavity fluids, blood, vascular tracts, abdominal neurofibrils, digestive tracts and digestive fluids while the inhibitor against the active substance is contained in the skin-mucous substances, skin and circular muscle layers. The chemical structure of these active substances is yet not made clear but is considered to be a kind of peptides, carbohydrato-peptides, metal-containing peptides, low molocular-weight proteases, nucleic acids, nucleic acid-like substances, carbohydrates or lipids.

The inventive medicament for thrombosis is prepared by the pulverization of living bodies of earthworms under such conditions as to deactivate the aforementioned inhibitor without decreasing the pharmacological activity of the above mentioned active substance.

The dirty matters of earthworms usually consist of the dirt sticking to the body surface and the fecal mud stagnating in the digestive tracts. Usually, wet living body of earthworms contains from 10 to 40% by weight of the former materials and about 10 to 15% by weight of the latter materials.

When pulverization of earthworm living bodies is undertaken with these dirty matters unremoved, the powder thus obtained is liable to denaturation during storage to cause a decrease in the therapeutic effect or appearance of side effects. Therefore, it is essential in the invention that these dirty matters are removed from the earthworm body as completely as possible. Moreover, the treatment for the removal of the dirty matters should be finished within a time as short as possible since eventual deactivation of the active substances effective for thrombosis would be caused in the course of an unduly prolonged treatment.

The dirty matters in the earthworm bodies can be removed by dipping and keeping earthworms alive in neutral water or in weakly acidic water having a controlled pH of 3 to 6.5 kept at a temperature of 6° to 26° C. until substantially complete excretion of the fecal mud in the digestive tracts is attained. The time required for this treatment is 30 to 60 hours in neutral water and 0.1 to 5 hours in weakly acidic water. The temperature for the treatment here should be in the range from 6° to 26° C. or, preferably, from 8°- to 22° C. since the activity of earthworms becomes decreased so that the fecal mud cannot be excreted completely at a temperature higher or lower than the above mentioned range. This treatment should preferably be carried out in a dark place since movement of earthworms is more active in a dark place than under light. When the treatment is undertaken by using weakly acidic water, the pH of the water is controlled within a range of 3 to 6.5 by the addition of a small amount of an acid selected from inorganic acids such as phosphoric acid, sulfuric acid, hydrochloric acid and the like and organic acids such as acetic acid, citric acid, fumaric acid, lactic acid, maleic acid, malic acid, malonic acid, phthalic acid, succinic acid, tartaric acid and the like. These acids can be used either singly or as a combination of two kinds or more. Furthermore, combined use of an alkali hydroxide or various salts sometimes facilitates pH-controlling with an acid. The amount of these additives should preferably be limited not to exceed 2% by weight or, more preferably, not to exceed 1% by weight of the water.

In the treatment for the removal of the dirty matters, the time required for complete removal depends on the temperature of water in which the earthworms are immersed. Usually the treatment time is decreased by increasing the temperature. For instance, comparison of excretion rate of fecal mud was made between 8° C. and 15° C. by dipping 100 g of earthworms of a certain species in neutral underground water having a pH of 7.2 to give the results shown in Table 1.

TABLE 1

| Hours of immersion | At 15° C., % by weight I | | | | At 8°C., % by weight I | |
|---|---|---|---|---|---|---|
| | Group-A | Group-B | II | III | Group-C | Group-D |
| 4 | 6 | 5 | 5 | 5 | 2 | 2 |
| 10 | 21 | 18 | 19 | 20 | 6 | 6 |
| 16 | 46 | 44 | 45 | 45 | 18 | 18 |
| 20 | 70 | 68 | 70 | 70 | 35 | 34 |
| 24 | 88 | 86 | 86 | 87 | 60 | 61 |
| 28 | 96 | 93 | 95 | 95 | 79 | 78 |
| 32 | 99 | 98 | 98 | 98 | 90 | 89 |
| 36 | 100 | 100 | 100 | 100 | 94 | 94 |
| 40 | — | — | — | — | 98 | 98 |
| 44 | — | — | — | — | 100 | 100 |

I: *Lumbricus rubellus*
II: *Pheretima divergens*
III: *Eisenia foetida*

As is clear from this table, it was sufficient to keep earthworms in neutral water at 15° C. for 36 hours in order to attain 100% excretion of the fecal mud in the digestive tracts irrespective of the species of the earthworms including *Lumbricus rubellus*, *Pheretima communissima* and *Eisenia foetida*. Likewise, a length of about 44 hours was sufficient for *Lumbricus rubellus* by keeping in neutral water at 8° C. Thus, it is understood that the excretion time of fecal mud depends on the temperature of water.

In addition, the yields in % by weight of wet earthworms taken out from water and drained following 100% excretion of the fecal mud were 93% for both of Group-A and Group-B of *Lumbricus rebellus* 92.5 to 93% for *Pheretima communissima* or *Eisenia foetida* and 91% for Group-C and Group-D of *Lumbricus rubellus* relative to the weight of the untreated earthworms showing an increased loss of the body weight along with extension of the dipping time in water.

In contrast to the above, the time required for 100% excretion of the fecal mud in the digestive tracts was 130 minutes and the yield of the wet earthworm bodies after draining was 95% in an experiment in which each 100 g of grown-up earthworms of *Lumbricus rubellus* with cleaned body surface were dipped in a 500 ml bath of slightly acidified water having a pH of 6.0 prepared by the addition of either malic acid alone or a 1:1 by weight mixture of malic acid and citric acid at 15° C. in a similar manner as above.

In the prior art for the preparation of a dry powder of earthworms, the fecal mud in the digestive tracts of earthworms is conventionally removed by a mechanical method such as pressing or squeezing. A great decrease in the yield of active substances effective for medication of thrombosis is unavoidable in such a mechanical method since a large portion of the digestive fluids, body cavity fluids, blood and the like is simultaneously squeezed out together with the fecal mud. In the present invention, only useless fecal mud can be removed selectively by undertaking the above described method of spontaneous excretion.

Then, the living bodies of earthworms substantially completely freed from dirty matters according to the above described procedure are mashed to be converted into a mushy slurry or paste. In order to obtain a uniform paste by mashing, any suitable machines such as homogenizers, blenders, homomixers, grinding machines, pressurizable cell disintegrators and the like, for example, can be used. This mashing treatment is usually carried out at a temperature in the range from 1° to 15° C. or, preferably, from 2° to 15° C.

The mushy paste of earthworms thus obtained is then subjected to a drying treatment prior to pulverization. This drying treatment should preferably be carried out under vacuum in order to prevent a possible decrease in the content of the effective ingredient by a prolonged drying treatment. Usually, a pressure of 30 mmHg or lower is preferred as the pressure applied in this treatment. The drying treatment may be carried out by any of known methods including freeze-vacuum drying, room-temperature vacuum drying, high-temperature vacuum drying and combinations thereof but, in any event, should be carried out under such conditions that the temperature reaches 70° to 80° C. at the final stage. The following two methods are particularly preferred among the above mentioned drying methods.

Namely, the mushy paste of earthworms is frozen in the first method at a temperature not to exceed −5° C. or, preferably, at a low temperature of −10° C. to −60° C., and then, while keeping the pressure of the atmosphere at 1 mmHg or lower, the temperature is increased stepwise to reach 70° to 80° C. at the final stage within 20 to 72 hours.

In the second method, the mushy paste of earthworms is first subjected to a degassing treatment at a temperature of 0° to 30° C. under a pressure of 30 mmHg or lower either by standing without or with agitation followed by a stepwise increase of the temperature to reach 70° to 80° C. at the final stage within 5 to 30 hours so as to be dried while the pressure is kept not to exceed 1 mmHg.

In the prior art, washed and cleaned living bodies of earthworms as such are dried by heating at 80° to 90° C. under normal pressure as is taught in Japanese patent Kokai 58-126770 and 60-62965. Alternatively, one of the inventors has disclosed a method in Japanese patent Kokai 59-216572 according to which living bodies of earthworms after removal of excrements are mechanically ground into a mushy paste which is frozen and freeze-dried under a pressure of 0.1 to 0.3 mmHg by increasing the temperature stepwise from −40° to +80° C. and then keeping the temperature of 80° C. for at least 20 hours. Each of these prior art methods has a problem that the effective ingredient is unavoidably decomposed or dissipated so that the yield of the product would be decreased or the activity of the product is decreased. In the method of freeze-drying at a low temperature described in Acta Haematologica Japonica, volume 45, page 503 (1982), there may be a disadvantage that an unduly long time is taken for the treatment or denaturation of the once obtained dry powder by sundry germs may take place in the storage although decomposition and dissipation of the effective ingredients can effectively be prevented. In contrast thereto, deactivation of the inhibitor or the hemolytically active substances contained mainly in the skin or circular muscle layer is possible without being accompanied by the decomposition or dissipation of the effective ingredients contained mainly in the smooth muscular layer, body cavity fluid, blood and digestive tracts of earthworms by the above method with an additional advantage that denaturation after a long period of storage can be avoided owing to sterilization of sundry bacteria.

In particular, the second method has advantages including the remarkably decreased time taken for the treatment due to omission of the process of freeze-drying, high content of crude protein in the dried powder of earthworms thus obtained, excellent pharmocological activity and high absorption reaching 90 to 97% by the oral administration.

Naturally, the dried powder of earthworms obtained by any other methods can also be used as an effective component in the inventive medicament for thrombosis but such a powder must be used in an amount of 3 to 30 times of the amount of the dried powder obtained by the above-mentioned method.

The process of vacuum drying may be carried out by using a known apparatus including vacuum freeze-drying apparatuses, agitator-type vacuum-drying apparatuses and the like but the treatment is advantageously carried out by using a rotary vacuum-drying apparatus such as a double-cone type vacuum drying apparatus, a tumbler-type vacuum drying apparatus, rotary drum-type vacuum drying apparatus and the like in view of the possibility of continuous running and the high efficiency of drying.

In the following, a preferable way for practicing each of the above mentioned two methods is described.

In the first method, the mushy paste of earthworms is frozen at a temperature of −10° C. to −60° C. or, Preferably, −30° C. to −50° C. taking 10 to 60 hours followed by freeze-drying at this temperature for 5 to 12 hours under a vacuum of 0.01 to 0.2 mmHg. Then, the vacuum-drying is continued by increasing the temperature stepwise taking 5 to 15 hours at 20° to 30° C. under 0.01 to 0.2 mmHg, then 10 to 20 hours at 35° to 50° C. under 0.1 to 0.5 mmHg and finally 0.1 to 19 hours at 70° to 80° C. or, preferably, at 75° to 80° C. under 0.001 to 5 mmHg. In this manner, a germ-free dried powder of earthworms can be obtained in a yield of 20 to 35% by weight relative to the living earthworms.

In the second method, the mushy paste of earthworms is subjected to a degassing treatment under a pressure of 10 to 30 mmHg at a temperature of 0° to 30° C. for 0.5 to 5 hours and introduced into a rotary vacuum drying machine to be vacuum-dried successively under 0.001 to 5 mmHg at 10° to 40° C. for 1 to 10 hours, then under 0.001 to 5 mmHg at 40° to 50° C. for 2 to 15 hours and finally under 0.001 to 5 mmHg at 70° to 80° C. for 0.1 to 10 hours. In this manner, a germ-free dry powder of earthworms can be obtained in a yield of 20 to 35% by weight.

The dry powder of earthworms thus obtained is colored in yellow to brown and free from the problem of denaturation even after storage of six years or longer at 5° to 45° C. under a condition with sealing against atmospheric air.

The dry powder of earthworms obtained in the above described manner usually contains 10 to 11% by weight of moisture, 4 to 5% by weight of ash, 56 to 59% by weight of crude protein, 10 to 12% by weight of crude lipids, 0.05 to 0.5% by weight of crude fiber and 14 to 18% by weight of soluble non-nitrogenous substances. The nitrogenous ingredients thereof contain 18 amino acids including aspartic acid, threonine, serine, glutamic acid, proline, glycine, alanine, cystine, valine, methionine, isoleucine, leucine, tyrosine, phenylalanine, tryptophan, lysine, histidine and arginine. The amino acids as a whole typically consist of the respective amino acids each in a % fraction given below.

| aspartic acid | 6.5 to 7.5% by weight |
| threonine | 3.0 to 3.3% by weight |
| serine | 3.0 to 3.5% by weight |
| glutamic acid | 8.3 to 9.2% by weight |
| proline | 1.2 to 1.4% by weight |
| glycine | 3.3 to 3.6% by weight |
| alanine | 3.5 to 4.1% by weight |
| cystine | 0.5 to 0.7% by weight |
| valine | 3.3 to 3.6% by weight |
| methionine | 1.0 to 1.2% by weight |
| isoleucine | 3.0 to 3.2% by weight |
| leucine | 5.0 to 5.5% by weight |
| tyrosine | 2.3 to 2.7% by weight |
| phenylalanine | 2.7 to 3.0% by weight |
| tryptophan | 0.3 to 0.4% by weight |
| lysine | 4.8 to 5.3% by weight |
| histidine | 1.6 to 1.8% by weight |
| arginine | 4.2 to 4.6% by weight |

The amounts of the inorganic ingredients contained in 100 g of the dry powder of earthworms are typically as follows.

| Ca | 0.53 to 0.58 g |
| Mg | 0.26 to 0.29 g |
| K | 0.88 to 0.96 g |
| Na | 0.54 to 0.58 g |
| P | 0.71 to 0.76 g |
| Fe | 0.08 to 0.09 g |
| Cu | 2.3 to 2.5 mg |
| Zn | 7.5 to 8.1 mg |
| Mn | 2.1 to 2.3 mg |

The content of each of these ingredients varies somewhat depending on the conditions of drying. Generally, the powder prepared without freeze-drying contains more of crude protein and less inorganic substances as compared with that prepared by freeze-drying. For example, the content of crude protein in the freeze-dried powder is 57.5% by weight or smaller but at least 58.1% by weight in the non-freeze-dried powder.

The medicament form of the dry powder of earthworms for the administration of thrombotic patients may be either for oral administration or parenteral administration with preference to the former type. The medicament form for oral administration includes capsules, tablets, granules, powders, coated solid medicament forms, sugar-coated tablets, emulsions and the like prepared from the dry powder of earthworms alone or from a mixture of the same with a pharmacologically acceptable medicinal carrier.

The medicinal carrier usable includes excipients such as lactose, saccharose, mannitol, glucose, starch, sorbitol, glycine, calcium phosphate, microcrystalline cellulose and the like; binders such as starch, gelatine, gum arabic, glucose, saccharose, sorbitol, mannitol, tragacanth gum, hydroxypropyl cellulose, hydroxypropyl methyl cellulose, copolymers of 2-methyl-5-vinylpyridine, methacrylic acid and methyl or ethyl acrylate, polyvinyl pyrrolidone, sodium alginate and the like; lubricants such as stearic acid, hardened oils, magnesium stearate, calcium stearate, polyoxyethylene monostearate, talc, silicon dioxide, polyethylene glycol and the like; disintegrating agents such as potato starch and surfactant-containing starch; and moisturizing agents such as sodium laurylsulfate and the like. In addition, the medicament in the form of a suppository can also be used as a type of parenterally administrable medicament forms. Particularly suitable bases in the formulation of the suppository include cacao butter, Witepsol, Subanal, polyethylene glycol, polypropylene glycol, glycerogelatine, gelatine capsules and the like. Other optional additives include known antiseptics having no problem in safety such as methyl p-hydroxybenzoate, propyl p-hydroxybenzoate, butyl p-hydroxybenzoate, butyl hydroxyanisole and the like and coloring materials having safety.

Appropriate administration dose of the dry powder of earthworms as the inventive medicament for thrombosis depends on the method of administration and the age, body weight, condition and type of the disease of the patient but, usually, an amount of 0.001 g to 15 g per day is suitable. The most preferable dose is 0.002 g to 9 g per day which amount is administrated each day at one time or in three or less portions by dividing the amount.

As is described above in detail, the inventive medicament for thrombosis has advantages of prominent therapeutic efficiency for thrombosis or various kinds of diseases complicated with or related to thrombosis such as lipemia, hypertension and hypotonia without being accompanied by any side effects as well as long-term storability without denaturation. Moreover, the medicament for thrombosis according to the invention has an industrially important significance since it can be manufactured in a high yield from an inexpensive natural product as the raw material.

In the following, examples are given to describe the inventive medicament and the method for the preparation thereof in more detail.

EXAMPLE 1

About 2150 live earthworms of Lumbricus rubellus weighing 1 kg lightly washed with water were kept at 18° C. for 2 hours in a bath of 4 liters of acidified water having a pH of 6.2 as adjusted by the addition of a 1:1 by weight mixture of malic acid and citric acid so that the fecal mud in the digestive tracts was completely excreted. Thereafter, the live earthworms were thoroughly washed with water to remove the dirty matters adhering to the body surface.

In the next place, the earthworms were mashed in a mixer to prepare a mushy paste which was kept frozen on a tray at −40° C. for 40 hours followed by freeze-drying for 6 hours under a pressure of 0.1 mmHg at the same temperature. Thereafter, the temperature of the rack on which the tray was mounted was increased stepwise to continue the vacuum drying following the schedule of: 6 hours at 30° C. under 0.1 mmHg, then 10 hours at 50° C. under 0.2 mmHg and finally 8 hours at 80° C. under 0.2 mmHg. In this way, 280 g of a dry powder of earthworms were obtained as a product, which is referred to as the product W-1 hereinbelow.

EXAMPLE 2

Live earthworms of *Lumbricus rubellus* weighing 1 kg lightly washed with water were kept at 18° C. for 3 hours in a bath of 3 liters of water having a pH of 5.5 as adjusted by the addition of a 1:1:1 by weight mixture of phosphoric acid, tartaric acid and lactic acid so that the fecal mud in the digestive tracts was completely excreted. Thereafter, the live earthworms were thoroughly washed with water to remove the dirty matters adhering to the body surface.

In the next place, the earthworms were mashed in a mixer to prepare a mushy paste which was kept frozen on a tray at −30° C. for 52 hours followed by freeze-drying for 7 hours under a pressure of 0.1 mmHg at a decreased temperature of −35° C. Thereafter, the temperature of the rack on which the tray was mounted was increased stepwise to continue the vacuum drying following the schedule of: 10 hours at 28° C. under 0.1 mmHg, then 13 hours at 40° C. under 0.2 mmHg and finally 1 hour at 80° C. under 0.1 mmHg. In this way, 277 g of a dry powder of earthworms were obtained as a product, which is referred to as the product W-2 hereinbelow.

EXAMPLE 3

Live earthworms of Lumbricus rubellus weighing 1 kg lightly washed with water were kept at 15° C. for 36 hours in 3 liters of neutral water so that the fecal mud in the digestive tracts was completely excreted. Thereafter, the live earthworms were thoroughly washed with water to remove the dirty matters adhering to the body surface.

In the next place, the earthworms were mashed in an ultrahomomixer to prepare a mushy paste which was kept frozen on a tray at −45° C. for 45 hours followed by freeze-drying for 6 hours under a pressure of 0.1 mmHg at a decreased temperature of −45° C. Thereafter, the temperature of the rack on which the tray was mounted was increased stepwise to continue the vacuum drying following the schedule of: 10 hours at 30° C. under 0.1 mmHg, then 15 hours at 40° C. under 0.2 mmHg and finally 3 hours at 78° C. under 0.1 mmHg. In this way, 240 g of a dry powder of earthworms were obtained as a product, which is referred to as the product W-3 hereinbelow.

EXAMPLE 4

Live earthworms of *Lumbricus rubellus* weighing 1 kg lightly washed with water were kept at 15° C. for 3 hours in 2 liters of water having a pH of 5.8 as adjusted by the addition of malic acid so that the fecal mud in the digestive tracts was completely excreted. Thereafter, the live earthworms were thoroughly washed with water to remove the dirty matters adhering to the body surface.

In the next place, the earthworms were mashed in an ultrahomomixer to prepare a mushy paste which was kept frozen on a tray at −30° C. for 30 hours followed by freeze-drying for 8 hours under a pressure of 0.1 mmHg at the same temperature of −30° C. Thereafter, the temperature of the rack on which the tray was mounted was increased stepwise to continue the vacuum drying following the schedule of: 7 hours at 25° C. under 0.1 mmHg, then 12 hours at 45° C. under 0.1 mmHg and finally 7 hours at 80° C. under 0.1 mmHg. In this way, 275 g of a dry powder of earthworms were obtained as a product, which is referred to as the product W-4 hereinbelow.

EXAMPLE 5

Live earthworms of *Lumbricus rubellus* weighing 1 kg were washed five times with water to remove the mud, straw dusts and the like on the body surface and then kept at 12° C. for 42 hours in 2.5 liters of neutral water so that the fecal mud in the digestive tracts was completely excreted. Thereafter, the live earthworms were lightly washed with water and mashed in an ultrahomomixer to prepare a mushy paste which was kept frozen on a tray at −40° C. for 44 hours and then freeze-dried for 5 hours at −40° C. under a pressure of 0.1 mmHg. Thereafter, vacuum-drying of the paste was performed by increasing the temperature of the rack on which the tray was mounted stepwise following the schedule of: 8 hours at 25° C. under 0.1 mmHg, then 12 hours at 45° C. under 0.1 mmHg and finally 2 hours at 80° C. under 0.1 mmHg. In this way, 235 g of a dry powder of earthworms were obtained as a product, which is referred to as the product W-5 hereinbelow.

EXAMPLE 6

Live earthworms of *Lumbricus rubellus* weighing 1 kg were washed four times with water to remove the mud, feces and the like on the body surface and then kept at 15° C. for 2.5 hours in 2.5 liters of water having a pH of 5.7 as adjusted by the addition of a 1:1 by weight mixture of malic acid and lactic acid so that the fecal mud in the digestive tracts was completely excreted. Thereafter, the live earthworms were lightly washed with water and mashed in a mixer to prepare a mushy paste which was kept frozen on a tray at −35° C. for 24 hours and then freeze-dried for 7 hours at −35° C. under a pressure of 0.1 mmHg. Thereafter, vacuum-drying of the paste was performed by increasing the temperature of the rack on which the tray was mounted stepwise following the schedule of: 10 hours at 22° C. under 0.1 mmHg, then 10 hours at 42° C. under 0.2 mmHg and finally 3 hours at 78° C. under 0.1 mmHg. In this way, 270 g of a dry powder of earthworms were obtained as a product, which is referred to as the product W-6 hereinbelow.

EXAMPLE 7

Live earthworms of *Lumbricus rubellus* weighing 1 kg lightly washed with water were kept at 15° C. for 2.5 hours in 2.5 liters of water having a pH of 5.8 as adjusted by the addition of citric acid and containing 1.5 g of potassium dihydrogen phosphate so that the fecal mud in the digestive tracts was completely excreted. Thereafter, the live earthworms were washed with water to remove the dirty matters on the body surface and mashed in a mixer to prepare a mushy paste which was subjected to a degassing treatment in a rotary vacuum drier at 5° C. for 1 hour under a reduced pressure of 20 mmHg. Running of the drier was further continued and the mushy paste was vacuum-dried at −30° C. for 5 hours under a pressure of 0.2 mmHg. Thereafter, vacuum-drying of the paste was performed by increasing the temperature of the drier stepwise keeping the temperature first at 40° to 45° C. for 10 hours under 0.2 mmHg and then at 78° to 80° C. for 2 hours under 0.2 mmHg. In this way, 285 g of a dry powder of earthworms were obtained as a product, which is referred to as the product W-7 hereinbelow.

EXAMPLE 8

Live earthworms of *Lumbricus rubellus* weighing 1000 kg lightly washed with water were kept at 18° C. for 2 hours in 3000 liters of water having a pH of 6.0 as adjusted by the addition of malic acid so that the fecal mud in the digestive tracts was completely excreted. Thereafter, the live earthworms were washed with water at 5° C. to remove the dirty matters on the body surface and mashed in a homogenizer to prepare a mushy paste which was subjected to a degassing treatment with agitation at 10° C. for 2 hours under a reduced pressure of 20 mmHg. The degassed mushy paste was introduced into a first rotary vacuum drier and dried there at −35° C. for 4 hours under a pressure of 0.2 mmHg. The half-dried paste was transferred into a second and third rotary vacuum driers successively and dried there at 45° to 50° C. for 15 hours under 0.1 mmHg and at 80° C. for 2 hours under 0.2 mmHg, respectively. In this way. 283 kg of a dry powder of earthworms were obtained as a product, which is referred to as the product W-8 hereinbelow.

EXAMPLE 9

Live earthworms of *Lumbricus terrestris* weighing 1 kg were washed with water to remove the dirty matters on the body surface and then kept at 16° C. for 2.5 hours in 3 liters of water having a pH of 5.7 as adjusted by the addition of a 1:1 by weight mixture of malic acid and succinic acid and containing 1 g of sodium acetate and 0.5 g of sodium sulfate dissolved therein so that the fecal mud in the digestive tracts was completely excreted. Thereafter, the live earthworms were washed with water to remove the dirty matters on the body surface and mashed in a homogenizer to prepare a mushy paste which was subjected to a degassing treatment in a rotary vacuum drier at 15° C. for 1 hour under a reduced pressure of 25 mmHg. Running of the drier was further continued and the mushy paste was vacuum-dried at −30° C. for 4 hours under a pressure of 1.2 mmHg. Thereafter, vacuum-drying of the paste was performed by increasing the temperature of the drier stepwise keeping the temperature first at 45° to 50° C. for 18 hours under 0.2 mmHg and then at 78° to 80° C. for 2 hours under 0.2 mmHg. In this way, 280 g of a dry powder of earthworms were obtained as a product, which is referred to as the product W-9 hereinbelow.

EXAMPLE 10

Live earthworms of *Eisenia foetida* weighing 1 kg were washed with water to remove the dirty matters on the body surface and then kept at 20° C. for 1.5 hours in 2.5 liters of water having a pH of 6.0 as adjusted by the addition of a 1:1 by weight mixture of malic acid and citric acid so that the fecal mud in the digestive tracts was completely excreted. Thereafter, the live earthworms were washed with water to remove the dirty matters on the body surface and mashed in a blender to prepare a mushy paste which was subjected to a degassing treatment in a rotary vacuum drier at 8° C. for 2 hours under a reduced pressure of 20 mmHg. Running of the drier was further continued and the mushy paste was vacuum-dried at −30° C. for 3 hours under a pressure of 0.3 mmHg. Thereafter, vacuum-drying of the paste was performed by increasing the temperature of the drier stepwise keeping the temperature first at 43° to 45° C. for 15 hours under 0.2 mmHg and then at 75° to 80° C. for 1.5 hours under 0.2 mmHg. In this way, 270 g of a dry powder of earthworms were obtained as a product, which is referred to as the product W-10 hereinbelow.

EXAMPLE 11

Live earthworms of *Pheretima agrestis* belonging to the family of *Magascolecidae* weighing 1 kg were thoroughly washed with water to remove the dirty matters on the body surface and then kept at 17° C. for 2 hours in 2.5 liters of water having a pH of 5.9 as adjusted by the addition of a 1:1 by weight mixture of malic acid and tartaric acid so that the fecal mud in the digestive tracts was completely excreted. Thereafter, the live earthworms were washed with water to remove the dirty matters on the body surface and mashed in a homogenizer to prepare a mushy paste which was subjected to a degassing treatment in a rotary vacuum drier at 10° C. for 2 hours under a reduced pressure of 20 mmHg. Running of the drier was further continued and the mushy paste was vacuum-dried at −35° C. for 3 hours under a pressure of 0.2 mmHg. Thereafter, vacuum-drying of the paste was performed by increasing the temperature of the drier stepwise keeping the temperature first at 40° to 45° C. for 13 hours under 0.2 mmHg and then at 75° to 80° C. for 3 hours under 0.2 mmHg. In this way, 265 g of a dry powder of earthworms were obtained as a product, which is referred to as the product W-11 hereinbelow.

EXAMPLE 12

Live earthworms of *Pheretima communissima* weighing 1 kg were thoroughly washed with water to remove the dirty matters on the body surface and then kept at 10° C. for 40 hours in a bath of 3 liters of fresh underground water so that the fecal mud in the digestive tracts was completely excreted. Thereafter, the live earthworms were washed with water to remove the dirty matters on the body surface and mashed in a homogenizer to prepare a mushy paste which was subjected to a degassing treatment at 10° C. for 3 hours under a reduced pressure of 22 mmHg. The degassed mushy paste was introduced into a rotary vacuum drier and vacuum-dried there at −28° C. for 5 hours under a pressure of 0.3 mmHg. Thereafter, vacuum-drying of the paste was performed by increasing the temperature of the drier stepwise keeping the temperature first at 40° to 45° C. for 12 hours under 0.2 mmHg and then at 75° to 80° C. for 5 hours under 0.1 mmHg. In this way, 238 g of a dry powder of earthworms were obtained as a product, which is referred to as the product W-12 hereinbelow.

EXAMPLE 13

Live earthworms of *Lumbricus rubellus* weighing 1 kg were kept at 15° C. for 40 hours in a bath of 4 liters of fresh underground water so that the fecal mud in the digestive tracts was completely excreted. Thereafter, the live earthworms were washed with water to remove the dirty matters on the body surface and mashed in a mixer to prepare a mushy paste which was subjected to a degassing treatment in a rotary vacuum drier at 10° C. for 1 hour under a reduced pressure of 20 mmHg. The degassed mushy paste was vacuum-dried by continuously running the drier at −35° C. for 4 hours under a pressure of 0.2 mmHg. Thereafter, vacuum-drying of the paste was performed by increasing the temperature of the drier stepwise keeping the temperature first at 40° to 45° C. for 12 hours under 0.2 mmHg and then at 75° to 78° C. for 3 hours under 0.2 mmHg. In this way, 260 g of a dry powder of earthworms were obtained as a product, which is referred to as the product W-13 hereinbelow.

EXAMPLE 14

Live earthworms of *Helodrilus foetidus* weighing 1 kg were gently stirred at 20° C. for 30 minutes in 2.5 liters of water having a pH of 5.8 as adjusted with malic acid so that the fecal mud in the digestive tracts was completely excreted along with removal of the dirty matters on the body surface. Thereafter, the live earthworms were washed with water and mashed to prepare a mushy paste which was put on a tray and kept for 48 hours in a freezer at −30° C. The frozen mushy paste was transferred into a vacuum freeze-drier and subjected to freeze-drying at −40° C. for 14 hours under a pressure of 0.1 mmHg. Thereafter, vacuum-drying of the paste was performed by increasing the temperature of the drier stepwise keeping the temperature first at 25° C. for 7 hours under 0.1 mmHg, then at 40° C. for 10 hours under 0.1 mmHg and finally at 80° C. for 4 hours under 0.3 mmHg. In this way, 225 g of a dry powder of earthworms were obtained as a product, which is referred to as the product W-14 hereinbelow.

EXAMPLE 15

Live earthworms of *Lumbricus rubellus* weighing 1 kg were gently stirred at 20° C. for 40 minutes in 2.5 liters of an aqueous solution having a pH of 5.6 as prepared by mixing 1250 ml of a 0.1M aqueous solution of potassium hydrogen phthalate and 970 ml of a 0.1M aqueous solution of sodium hydroxide with addition of pure water to make up the volume so that the fecal mud in the digestive tracts was completely excreted. Thereafter, the live earthworms were washed with water to remove the dirty matters on the body surface and mashed in a mixer to prepare a mushy paste which was put on a tray in a layer having a thickness of 25 mm and kept for 30 hours in a freezer at −30° C. The frozen mushy paste was then transferred into a vacuum freeze-drier and subjected to freeze-drying at −35° C. for 10 hours under a pressure of 0.2 mmHg. Thereafter, vacuum-drying of the paste was performed by increasing the temperature of the drier stepwise keeping the temperature first at 40° to 41° C. for 20 hours under 0.2 mmHg and then at 78° to 80° C. for 2 hours under 0.1 mmHg. In this way, 205 g of a dry powder of earthworms were obtained as a product, which is referred to as the product W-15 hereinbelow.

EXAMPLE 16

Live earthworms of *Lumbricus rubellus* weighing 1 kg were gently stirred at 19° C. for 40 minutes in 3.0 liters of an aqueous solution having a pH of 5.8 as prepared by mixing 1500 ml of a 0.1M aqueous solution of potassium dihydrogen phosphate and 108 ml of a 0.1M aqueous solution of sodium hydroxide with addition of pure water to make up the volume so that the fecal mud in the digestive tracts was completely excreted along with removal of the dirty matters on the body surface. Thereafter, the live earthworms were washed with water and dried for 6 hours in the shade. The thus damp-dried earthworms were mashed and introduced into a rotary vacuum drier in which the mashed earthworms were subjected to a degassing treatment at 20° C. for 1 hour under a pressure of 20 mmHg. Thereafter, vacuum-drying of the mashed earthworms was performed by increasing the temperature of the drier stepwise keeping the temperature first at 40° C. for 10 hours under 0.2 mmHg and then at 79° to 80° C. for 8 hours under 0.1 mmHg. In this way, 195 g of a dry powder of earthworms were obtained as a product, which is referred to as the product W-16 hereinbelow.

EXAMPLE 17

Live earthworms of *Lumbricus rubellus* weighing 1 kg were gently stirred at 18° C. for 40 minutes in 3.0 liters of an aqueous solution having a pH of 5.0 as prepared by mixing 1500 ml of a 0.1M aqueous solution of potassium hydrogen phthalate and 678 ml of a 0.1M aqueous solution of potassium hydroxide with addition of pure water to make up the volume so that the fecal mud in the digestive tracts was completely excreted along with removal of the dirty matters on the body surface. Thereafter, the live earthworms were washed with water and dried in the shade. The thus damp-dried earthworms were mashed and introduced into a rotary vacuum drier in which the mashed earthworms were subjected to degassing at 20° C. for 2 hours under a pressure of 20 mmHg. The thus degassed powder of earthworms was vacuum-dried at 30° to 35° C. for 5 hours under 0.2 mmHg and then at 78° to 80° C. for 6 hours under 0.2 mmHg. In this way, 190 g of a dry powder of earthworms were obtained as a product, which is referred to as the product W-17 hereinbelow.

EXAMPLE 18

Cultured earthworms of Eisenia foetida were washed with water and kept in a dark place at 15° C. for 24 hours so that about 50% of the fecal mud in their bodies was excreted. The live earthworms weighing 1 kg were then kept at 15° C. for 2 hours in 2 liters of water having a pH of 5.8 as adjusted with addition of malic acid so that the remaining fecal mud was completely excreted. Thereafter, the live earthworms were washed with water to remove the dirty matters on the body surface and mashed in an ultrahomomixer to prepare a mushy paste which was put on a tray and kept for 30 hours in a freezer at −30° C. The frozen mushy paste was subjected to freeze-drying at −30° C. for 30 hours under a pressure of 0.1 mmHg. Thereafter, vacuum-drying of the paste was performed by increasing the temperature of the tray stepwise keeping the temperature first at 25° C. for 7 hours under 0.1 mmHg, then at 45° C. for 5 hours under 0.1 mmHg and finally at 78° to 80° C. for 2 hours under 0.2 mmHg. In this way, 260 g of a dry powder of earthworms were obtained as a product, which is referred to as the product W-18 hereinbelow.

EXAMPLE 19

Cultured earthworms of Helodrilus fetidus were washed with water and kept in a dark place at 15° C. for 24 hours so that about 50% of the fecal mud in their bodies was excreted. The live earthworms weighing 1 kg were then kept at 15° C. for 1 hour in 2 liters of water having a pH of 5.7 as adjusted by the addition of a 1:1 by weight mixture of malic acid and citric acid so that the remaining fecal mud was completely excreted. Thereafter, the live earthworms were washed with water to remove the dirty matters on the body surface and mashed in a mixer to prepare a mushy paste which was introduced into a rotary vacuum drier and degassed there at 10° C. for 2 hours under a pressure of 22 mmHg. Running of the drier was continued to freeze-dry the paste at −30° C. for 5 hours under a pressure of 0.2 mmHg. Thereafter, vacuum-drying of the paste was performed by increasing the temperature of the drier stepwise keeping the temperature first at 40° C. for 10 hours under 0.2 mmHg and then at 78° to 80° C. for 2 hours under 0.2 mmHg. In this way, 265 g of a dry powder of earthworms were obtained as a product, which is referred to as the product W-19 hereinbelow.

REFERENCE EXAMPLE 1

Tables 2 and 3 given below show the results of the analyses for the nutrient composition and inorganic materials and amino acids in the crude protein, respectively, undertaken with the dry powders of earthworms W-2, W-4, W-7, W-8, W-10 and W-12 prepared in the above described Examples.

TABLE 2

| Dry powders of earthworms | | W-2 | W-4 | W-7 | W-8 | W-10 | W-12 |
|---|---|---|---|---|---|---|---|
| Composition, % by weight | Moisture | 10.6 | 10.6 | 10.1 | 10.2 | 10.2 | 10.8 |
| | Crude protein | 56.9 | 56.2 | 58.1 | 58.7 | 58.1 | 58.1 |
| | Crude lipids | 10.3 | 10.8 | 11.2 | 11.5 | 11.4 | 11.8 |
| | Soluble non-nitrogenous substances | 17.3 | 17.5 | 15.8 | 14.7 | 15.4 | 17.6 |
| | Ash | 4.8 | 4.8 | 4.7 | 4.8 | 4.8 | 4.7 |
| | Crude fiber | 0.1 | 0.1 | 0.1 | 0.1 | 0.1 | 0.1 |
| inorganic materials, mg/100 g | Ca | 553 | 554 | 539 | 551 | 552 | 543 |
| | Mg | 274 | 272 | 261 | 269 | 268 | 263 |
| | K | 921 | 992 | 889 | 912 | 914 | 902 |
| | Na | 559 | 557 | 543 | 553 | 556 | 548 |
| | P | 736 | 738 | 718 | 732 | 730 | 725 |
| | Fe | 85 | 85 | 84 | 84 | 82 | 83 |
| | Cu | 2.39 | 2.41 | 2.32 | 2.37 | 2.34 | 2.33 |
| | Zn | 7.73 | 7.78 | 7.53 | 7.67 | 7.62 | 7.58 |
| | Mn | 2.14 | 2.12 | 2.11 | 2.12 | 2.12 | 2.16 |

TABLE 3

| Dry powders of earthworms | | W-2 | W-4 | W-7 | W-8 | W-10 | W-12 |
|---|---|---|---|---|---|---|---|
| Amino acids, g/100 g | Aspartic acid | 7.11 | 7.03 | 7.28 | 7.35 | 7.27 | 6.88 |
| | Threonine | 3.21 | 3.17 | 3.28 | 3.30 | 3.28 | 3.09 |
| | Serine | 3.27 | 3.22 | 3.33 | 3.38 | 3.29 | 3.16 |
| | Glutamic acid | 8.77 | 8.64 | 8.98 | 9.04 | 8.97 | 8.49 |
| | Proline | 1.27 | 1.26 | 1.30 | 1.31 | 1.31 | 1.24 |
| | Glycine | 3.47 | 3.42 | 3.54 | 3.58 | 3.55 | 3.33 |
| | Alanine | 3.88 | 3.83 | 3.95 | 4.01 | 3.95 | 3.78 |
| | Cystine | 0.57 | 0.56 | 0.56 | 0.59 | 0.55 | 0.56 |
| | Valine | 3.42 | 3.39 | 3.50 | 3.58 | 3.52 | 3.32 |
| | Methionine | 1.03 | 1.01 | 1.05 | 1.06 | 1.04 | 1.01 |
| | Isoleucine | 3.08 | 3.04 | 3.18 | 3.18 | 3.16 | 3.01 |
| | Leucine | 5.26 | 5.18 | 5.34 | 5.43 | 5.36 | 5.02 |
| | Tyrosine | 2.53 | 2.50 | 2.60 | 2.59 | 2.58 | 2.42 |
| | Phenylalanine | 2.85 | 2.82 | 2.94 | 2.96 | 2.92 | 2.78 |
| | Tryptophan | 0.33 | 0.32 | 0.34 | 0.34 | 0.34 | 0.33 |
| | Lysine | 5.04 | 4.99 | 5.16 | 5.21 | 5.14 | 4.83 |
| | Histidine | 1.72 | 1.70 | 1.77 | 1.78 | 1.75 | 1.68 |
| | Arginine | 4.42 | 4.35 | 4.51 | 4.55 | 4.50 | 4.22 |

The analytical results shown in these tables indicate that the dry powders of earthworms contain crude protein, crude lipids and various kinds of metallic elements in high contents and that the contents of the essential amino acids are high in the amino acid composition of the crude protein. It is also noted that each of the dry powder products of earthworms W-7, W-8, W-10 and W-12 prepared by the process involving no step of freeze-drying contains the crude protein in a higher content and inorganic materials in a lower content than in the products prepared via freeze-drying. This is presumably due to the decrease in the loss of the effective ingredients as a consequence of the shortened time taken for the drying treatment.

REFERENCE EXAMPLE 2

Following are the results of the in vivo and in vitro tests for the Pharmacological activity of the dry powder products of earthworms prepared in the Examples.

I. Acute toxicity test

Animal tests were conducted for the acute toxicity of the 15 dry powdery products of earthworms prepared in the Examples including W-1 through W-4, W-6 through W-14, W-18 and W-19.

Thus, five a group of male mice of the ddy lineage each having a body weight of 30±2 g and five a group of rats of the Wister lineage each having a body weight of 100±2 g were compulsorily administrated orally with the powder in a dose of 0.1 to 5 g/kg and 2 to 8 g/kg, respectively, and they were raised at 22° to 23° C. under observation for 14 days after the oral administration. The result was that no animals died irrespective of the dose. Absolutely no difference was noted in the continued observation in the lapse of time relative to the appearance of intoxication and abnormality in behavior between the test animals and control animals. Almost no difference was found in the rate of body weight increase between the test and control animals. Absolutely no visible abnormality could be detected in any of the principal organs of the test animals in the autopsy undertaken after the end of the above mentioned test period. The above described extremely low toxicity of the earthworm powders gave no possibility of determining the value of $LD_{50}$.

II. Thrombi-dissolution test

Each of the same 15 dry powder products of earthworms as used in the acute toxicity test was suspended in 10 times by weight of physiological salt solution and agitated for 2 hours at 30° C. After settling of the powder, the supernatant was taken and used in the test. Thus, each of the sample solutions was subjected to the determination of the fibrinolytic activity in blood when it is administrated to human by using a plasminogen-free plate prepared by the method of Matsuda et al. (Thrombosis Res., volume 1, pages 619–630, 1972) according to the procedure of the standard fibrin plate method of Astrop and Miillertz (Arch. Biochem. Biophys., volume 40, pages 346–351, 1952). The results are shown in Table 4 below.

TABLE 4

| Sample | Dissolved area of standard fibrin plate, mm² |
|---|---|
| W-1 | 310 |
| W-2 | 310 |
| W-3 | 280 |
| W-4 | 300 |
| W-6 | 290 |
| W-7 | 350 |
| W-8 | 340 |
| W-9 | 340 |
| W-10 | 330 |
| W-11 | 330 |
| W-12 | 340 |
| W-13 | 350 |
| W-14 | 290 |
| W-18 | 290 |
| W-19 | 330 |

As is clear from this table, each of the dry powder products of earthworms exhibited excellent fibrinolytic activity. In particular, higher fibrinolytic activity was obtained with the products W-7 through W-13 and W-19 prepared in a process involving no step of freeze-drying than with the other products.

III. Hemolysis test

Each of nine dry powder products of earthworms including W-1, W-2 and W-4 through W-10 was suspended in 5 times by weight of physiological salt solution and the suspension was kept for 24 hours in a refrigerator at 5° C. followed by filtration under suction to give a filtrate which was used as a water-extract solution.

Separately, each of the same nine kinds of the powdery products as above was suspended in 5 times by weight of ethyl alcohol or acetone and the suspension was kept standing for 24 hours at 15° to 20° C. followed by filtration under suction to give a filtrate from which the solvent was evaporated to dryness at 40° to 45° C. under reduced pressure. The residue was dissolved in a physiological salt solution containing 1% by weight of carboxymethyl cellulose to give a solution in a concentration of 30% by weight. They are referred to as the ethyl alcohol-extract solution and acetone-extract solution, respectively, hereinbelow.

The procedure for the test of hemolysis was as follows. Thus, blood was taken from the auricular vein of a mature rabbit having a body weight of about 3 kg and subjected to a defibrination treatment to give a defibrinated blood.

Each of the above prepared water-extract solutions, ethyl alcohol-extract solutions and acetone-extract solutions was diluted with a physioloical salt solution to have concentrations of 5%, 1%, 0.1%, 0.01%, 0.001% and 0.0001% by weight and a drop of the defibrinated blood of rabbit was added to each of the thus diluted test solutions in a small test tube of 5 ml capacity to examine the result of hemolysis after 1 hour of standing. The results were that none of the powdery products of earthworms tested exhibited hemolysis irrespective of the testing conditions.

REFERENCE EXAMPLE 3

Various medicament forms were prepared using the dry powder products of earthworms as the effective ingredient.

(1) Formulation I for capsules

| Powder product W-8 | 150 mg |
|---|---|
| Lactose | 28 mg |
| Microcrystalline cellulose | 47 mg |
| Mannitol | 10 mg |
| Corn starch | 10 mg |
| Polyvinyl pyrrolidone | 2 mg |
| Hydroxypropyl cellulose | 3 mg |
| Total | 250 mg |

All of the ingredients in the above given formulation excepting the hydroxypropyl cellulose were thoroughly blended in a fluidized granulator and a 5% aqueous solution of the hydroxypropyl cellulose as a binder was sprayed to the blend which was dried at low temperature and granulated. Capsule medicament was prepared by filling hard capsules each with 250 mg of the thus prepared granules (2) Formulation II for granules

| Powder product W-12 | 150 mg |
|---|---|
| Lactose | 20 mg |
| Microcrystalline cellulose | 60 mg |
| Corn starch | 15 mg |
| Hydroxypropyl cellulose | 5 mg |
| Total | 250 mg |

All of the ingredients in the above given formulation excepting the hydroxypropyl cellulose were thoroughly blended in a fluidized granulator and a 5% aqueous solution of the hydroxypropyl cellulose as a binder was sprayed to the blend which was dried at low temperature and granulated.

(3) Formulation III for granules

| Powder product W-9 | 100 mg |
|---|---|
| Mannitol | 10 mg |
| Microcrystalline cellulose | 85 mg |
| Carboxymethyl cellulose calcium | 2 mg |
| Magnesium stearate | 1.5 mg |
| Hardened oil | 1.5 mg |
| Total | 200.0 mg |

All of the ingredients in the above given formulation were thoroughly blended and the blend was granulated by using an extruder machine.

(4) Formulation IV for granules

| Powder product W-7 | 150 mg |
|---|---|
| Lactose | 53 mg |
| Corn starch | 39 mg |
| Potato starch | 2 mg |
| Talc | 3 mg |
| Magnesium stearate | 3 mg |
| Total | 250 mg |

All of the ingredients in the above given formulation were thoroughly blended and the blend was granulated by using an extruder machine.

(5) Formulation V for capsules

Hard capsules were each filled with 250 mg of the granules prepared according to the Formulation IV given above.

(6) Formulation VI for capsules

| Powder product W-11 | 150 mg |
|---|---|
| Calcium monohydrogen phosphate | 60 mg |
| Disodium monohydrogen phosphate | 10 mg |
| Mannitol | 28 mg |
| Magnesium stearate | 42 mg |
| Total | 250 mg |

All of the ingredients in the above given formulation were thoroughly blended and No. 1 gelatin capsules were filled each with 250 mg of the powder blend.

(7) Formulation VII for enteric tablets

| Powder product W-10 | 100 mg |
|---|---|
| Mannitol | 10 mg |
| Microcrystalline cellulose | 85 mg |
| Carboxymethyl cellulose calcium | 2 mg |
| Magnesium stearate | 1.5 mg |
| Hardened oil | 1.5 mg |
| Total | 200 mg |

All of the ingredients in the above given formulation were thoroughly blended and base tablets were prepared by tabletting the blend in a tabletting machine. The base tablets were provided with an enteric coating layer of the formulation consisting of 14.8 mg of hydroxypropyl cellulose phthalate, 2.3 mg of dioctyl phthalate, 2.3 mg of stearic acid and 0.6 mg of light silicon dioxide.

(8) Formulation VIII for powder

| Powder product W-13 | 150 mg |
|---|---|
| Mannitol | 50 mg |
| Corn starch | 50 mg |
| Total | 250 mg |

All of the ingredients in the above given formulation were thoroughly blended in a conical blender to give a powdery medicament.

(9) Formulation IX for powder

| Powder product W-8 | 150 mg |
|---|---|
| Calcium monohydrogen phosphate | 20 mg |
| Corn starch | 80 mg |
| Total | 250 mg |

All of the ingredients in the above given formulation were thoroughly blended in a conical blender to give a powdery medicament.

(10) Formulation X for capsules

| Powder product W-9 | 150 mg |
|---|---|
| Sodium laurylsulfate | 4 mg |
| Disodium monohydrogen phosphate | 1 mg |
| Mannitol | 93 mg |
| Magnesium stearate | 2 mg |
| Total | 250 mg |

All of the ingredients in the above given formulation were thoroughly blended and hard capsules were filled each with 250 mg of the powder blend.

(11) Formulation XI for capsules

| Powder product W-1 | 150 mg |
|---|---|
| Calcium monohydrogen phosphate | 60 mg |
| Disodium monohydrogen phosphate | 10 mg |
| Mannitol | 28 mg |
| Magnesium stearate | 2 mg |
| Total | 250 mg |

All of the ingredients in the above given formulation were thoroughly blended and hard capsules were filled each with 250 mg of the powder blend.

(12) Formulation XII for capsules

| Powder product W-6 | 150 mg |
|---|---|
| Sodium laurylsulfate | 2 mg |
| Disodium monohydrogen phosphate | 4 mg |
| Mannitol | 92 mg |
| Magnesium stearate | 2 mg |
| Total | 250 mg |

All of the ingredients in the above given formulation were thoroughly blended and hard capsules were filled each with 250 mg of the powder blend.

(13) Formulation XIII for tablets

| Powder product W-3 | 150 mg |
|---|---|
| Mannitol | 123 mg |
| Hydroxypropyl methyl cellulose | 7 mg |
| Talc | 5 mg |
| Microcrystalline cellulose | 60 mg |
| Hydrogenated castor oil | 5 mg |

-continued

| Total | 350 mg |
|---|---|

All of the ingredients in the above given formulation were thoroughly blended and the powder blend was tabletted in a tabletting machine.

(14) Formulation XIV for tablets

| Powder product W-4 | 150 mg |
|---|---|
| Corn starch | 60 mg |
| Lactose | 80 mg |
| Talc | 7 mg |
| Magnesium stearate | 3 mg |
| Total | 300 mg |

All of the ingredients in the above given formulation were thoroughly blended and the powder blend was tabletted in a tabletting machine.

(15) Formulation XV for tablets

| Powder product W-6 | 150 mg |
|---|---|
| Soluble starch | 20 mg |
| Corn starch | 125 mg |
| Microcrystalline cellulose | 45 mg |
| Silicon dioxide | 6 mg |
| Magnesium stearate | 4 mg |
| Total | 350 mg |

All of the ingredients in the above given formulation were thoroughly blended and the powder blend was tabletted in a tabletting machine.

(16) Formulation XVI for capsules

| Powder product W-14 | 150 mg |
|---|---|
| Sodium laurylsulfate | 3 mg |
| Disodium monohydrogen phosphate | 2 mg |
| Mannitol | 93 mg |
| Magnesium stearate | 2 mg |
| Total | 250 mg |

All of the ingredients in the above given formulation were thoroughly blended and No. 1 hard capsules were filled each with 250 mg of the powder blend.

(17) Formulation XVII for capsules

| Powder product W-15 | 150 mg |
|---|---|
| Lactose | 53 mg |
| Corn starch | 39 mg |
| Potato starch | 2 mg |
| Talc | 3 mg |
| Magnesium stearate | 3 mg |
| Total | 250 mg |

All of the ingredients in the above given formulation were thoroughly blended and the powder blend was granulated using an extruder machine. Hard capsules were filled each with 250 mg of the granules.

(18) Formulation XVIII for capsules

| Powder product W-16 | 150 mg |
|---|---|
| Calcium monohydrogen phosphate | 40 mg |
| Disodium monohydrogen phosphate | 10 mg |
| Mannitol | 48 mg |

-continued

| Magnesium stearate | 2 mg |
|---|---|
| Total | 250 mg |

All of the ingredients in the above given formulation were thoroughly blended and No. 1 gelatin capsules were filled each with 250 mg of the powder blend.

(19) Formulation XIX for capsules

| Powder product W-17 | 150 mg |
|---|---|
| Lactose | 28 mg |
| Microcrystalline cellulose | 47 mg |
| Mannitol | 10 mg |
| Corn starch | 10 mg |
| Polyvinyl pyrrolidone | 2 mg |
| Hydroxypropyl cellulose | 3 mg |
| Total | 250 mg |

All of the ingredients in the above given formulation excepting the hydroxypropyl cellulose were thoroughly blended in a fluidized granulator and a 5% aqueous solution of the hydroxypropyl cellulose as a binder was sprayed to the blend which was dried at low temperature and granulated. Capsule medicament was prepared by filling hard capsules each with 250 mg of the thus prepared granules.

(20) Formulation XX for capsules

| Powder product W-16 | 150 mg |
|---|---|
| Calcium monohydrogen phosphate | 60 mg |
| Disodium monohydrogen phosphate | 10 mg |
| Mannitol | 28 mg |
| Magnesium stearate | 2 mg |
| Total | 250 mg |

All of the ingredients in the above given formulation were thoroughly blended and No. 1 gelatin capsules were filled each with 250 mg of the powder blend.

(21) Formulation XXI for capsules

| Powder product W-19 | 150 mg |
|---|---|
| Sodium laurylsulfate | 4 mg |
| Disodium monohydrogen phosphate | 1 mg |
| Mannitol | 93 mg |
| Magnesium stearate | 2 mg |
| Total | 250 mg |

All of the ingredients in the above given formulation were thoroughly blended and gelatin capsules were filled each with 250 mg of the powder blend.

APPLICATION EXAMPLE 1

The medicament for thrombosis according to the present invention was orally administered to nine patients of thrombosis and related diseases and one healthy male person of 28 years old for control, of whom the blood pressure and the total cholesterol, referred to as TC hereinbelow, in mg/dl and total triglyceride, referred to as TG hereinbelow, in mg/dl in their serums were as shown in Table 5 below excepting the case No. 3.

The main symptoms in the nine patients were as follows.

Case No. 1 (male, age 54): hypertension, thormbosis, lipemia

Case No. 2 (female, age 34): hypertension, lipemia
Case No. 3 (male, age 43): deep-vein thrombosis
Case No. 4 (female, age 44): deep-vein thrombosis, lipemia
Case No. 5 (female, age 40): ditto
Case No. 6 (male, age 42): hypotonia, lipemia
Case No. 7 (female, age 53): ditto
Case No. 8 (male, age 58): hypertension, thormbosis, lipemia
Case No. 9 (female, age 60): thrombosis, lipemia Blood was taken from each case before the start of the test and periodically during the test period and the blood plasma was subjected to the determination of the fibrin degradation products, referred to as FDp hereinbelow, and the tissular plasminogen activator, referred to as tPA hereinbelow, to give the results shown in Tables 6 and 7, respectively. Further, the blood pressure as well as TC and TG in the blood were determined after 25 days of administration for the control and patients excepting the case No. 3 to give the results shown in Table 5.

TABLE 6

| | FDP, ng/ml Days of administration | | | | | | | | | |
|---|---|---|---|---|---|---|---|---|---|---|
| Case No. | 0 | 1 | 2 | 3 | 4 | 11 | 13 | 15 | 18 | 25 |
| Control | 58 | 50 | 162 | 59 | 66 | — | — | 66 | — | 66 |
| 1 | 230 | 180 | 110 | 132 | 260 | — | — | 118 | — | 75 |
| 2 | 54 | 60 | 76 | — | 210 | — | 98 | — | 62 | 62 |
| 3 | 190 | 200 | 188 | 260 | 125 | 135 | — | — | 100 | 76 |
| 4 | 205 | 190 | 185 | 260 | 220 | 200 | — | — | 138 | 75 |
| 5 | 170 | 260 | 260 | — | 240 | — | — | 310 | — | 152 |
| 6 | 60 | 65 | 78 | 240 | 110 | — | 75 | — | 70 | 70 |
| 7 | 55 | 70 | 80 | 245 | 120 | — | 112 | — | 68 | 68 |
| 8 | 180 | 200 | 200 | 250 | 132 | — | — | 110 | — | 78 |
| 9 | 140 | 160 | 115 | 134 | 220 | — | — | 115 | — | 70 |

TABLE 7

| | tPA, ng/ml Days of administration | | | | | | | | | |
|---|---|---|---|---|---|---|---|---|---|---|
| Case No. | 0 | 1 | 2 | 3 | 4 | 11 | 13 | 15 | 18 | 25 |
| Control | 11.6 | 11.4 | 13.4 | 11.4 | 13.2 | — | — | 10.8 | — | 11.2 |
| 1 | 13.6 | 14.8 | 11.6 | 10.2 | 16.2 | — | — | 10.8 | — | 11.0 |
| 2 | 9.8 | 9.0 | 11.2 | — | 13.6 | — | 9.3 | — | 10.2 | 10.5 |
| 3 | 12.8 | 13.8 | 13.4 | 17.4 | 15.4 | 16.0 | — | — | 16.8 | 13.9 |
| 4 | 12.4 | 10.4 | 11.2 | 17.6 | 16.6 | 16.4 | — | — | — | 13.8 |
| 5 | 8.6 | 7.6 | 6.6 | — | 5.4 | — | — | 11.0 | — | 7.0 |
| 6 | 10.5 | 10.0 | 12.1 | 14.8 | 11.4 | — | 10.2 | — | 10.8 | 10.9 |
| 7 | 10.4 | 10.0 | 11.8 | 14.8 | 11.5 | — | 9.8 | — | 10.4 | 10.5 |
| 8 | 12.8 | 12.2 | 12.2 | 17.4 | 14.0 | — | — | 16.2 | — | 10.2 |
| 9 | 11.2 | 12.5 | 11.8 | 11.8 | 15.4 | — | — | 12.2 | — | 10.8 |

TABLE 5

| | Before start of test | | | | After 25 days of administration | | | |
|---|---|---|---|---|---|---|---|---|
| | Blood pressure, mmHg | | Lipids in serum, mg/dl | | Blood pressure, mmHg | | Lipids in serum, mg/dl | |
| Case No. | Maximum | Minimum | TC | TG | Maximum | Minimum | TC | TG |
| Control | 137 | 80 | 185 | 135 | 135 | 80 | 180 | 115 |
| 1 | 150 | 95 | 258 | 197 | 134 | 80 | 208 | 160 |
| 2 | 150 | 100 | 240 | 182 | 135 | 82 | 198 | 152 |
| 4 | — | — | 260 | 200 | — | — | 210 | 160 |
| 5 | — | — | 245 | 185 | — | — | 225 | 170 |
| 6 | 112 | 60 | 232 | 194 | 128 | 77 | 198 | 155 |
| 7 | 110 | 60 | 252 | 200 | 130 | 76 | 206 | 163 |
| 8 | 160 | 110 | 250 | 205 | 143 | 88 | 210 | 168 |
| 9 | 152 | 90 | 240 | 193 | 135 | 85 | 210 | 155 |

Thus, each of the cases and the control was orally administrated three times a day after each meal with one capsule containing 150 mg of the dry powder of earthworms prepared in the above described formulations, i.e. Formulation I for the control and the cases No. 1 to No. 5, Formulation VI for the case No. 6, Formulation X for the case No. 7, Formulation XI for the case No. 8 and Formulation XII for the case No. 9, over 25 days. The cases No. 3, No. 4 and No. 5 were administrated with an anticoagulant Warfalin potassium concurrently with the capsuled medicament under testing.

As is shown by these results, the medicament under testing had an effect in the case No. 2 suffering complication of hypertension and lipemia and No. 6 and No. 7 suffering complication of hypotonia and lipemia to temporarily increase the value of FDP by about 4 times from the initial value of 54 to 60 ng/ml within 2 to 4 days of administration but the initial value of FDP was regained by 18 days of administration and thereafter indicating dissolution of the fibrin deposited on the vein walls so as to establish a healthy condition of the veins by the oral administration of the dry powder of earthworms. In addition, the administration of the medicaments in these patients was also effective therapeutically to establish normal values of the blood pressure and the TC and TG in the blood.

In the cases No. 3 suffering deep-vein thrombosis, No. 4 suffering complication of deep-vein thrombosis and lipemia, No. 1 and No. 8 suffering complication of thrombosis, hypertension and lipemia and No. 9 suffering complication of thrombosis and lipemia, the value of FDP, which was 140 to 230 ng/ml before the start of the test, fell to the normal level as in healthy persons though with some variation at the initial stage of the administration test. These results indicate that, along with dissolution of fibrin, improvement can be obtained by the administration of the medicament in the symptoms of metabolic inhibition of the vein walls and thrombosis caused by the enhancement of the blood coagulation and remarkable decrease in the fibrinolytic activity. In the cases No. 1 and No. 8 suffering complication of thrombosis, hypertension and lipemia and No. 2 suffering complication of hypertension and lipemia, normal values of the blood pressure and TC and TG in the blood could be established by the administration of the dry powder of earthworms.

In the case No. 5 suffering complication of deep-vein thrombosis and lipemia, on the other hand, the value of FDP indicated a trend of gradual decrease by the administration of the dry powder of earthworms with repetition of fluctuation to higher and lower values but no normal value of FDP could be established even by the administration of the medicament for 25 days. It would be a fair expectation, however, that further continued administration would be effective to completely cure the complication of deep-vein thrombosis and lipemia.

As to the value of tPA, a trend of sustained increase was noted in each case by the administration of the dry powder of earthworms. This trend was more remarkable on the third to fourth days and thereafter from the start of the administration test. In particular, the values of FDP and tPA attained the respective maximum values simultaneously on the third or fourth days and thereafter from the start of the administration test. It would be a fair presumption of the mechanism from these results that the value of tPA in the plasma is increased by the oral administration of the dry powder of earthworms consequently to promote dissolution of fibrin lumps.

APPLICATION EXAMPLE 2

It is a known fact that, when a thrombolytic enzyme such as urokinase is administrated to a patient by intravenous injection, the activated partial thromboplastin time, referred to as aPTT hereinbelow, is shortened during the administration period to cause an increased tendency toward hemorrhage as a consequence of decomposition of the fibrinogen, referred to as Fibgn hereinbelow.

In view of the above mentioned fact, each of five patients including cases No. 10 to No. 14 and one healthy male person of 30 years old as a control was orally administrated three times a day after each meal with one capsule prepared according to the above described Formulation 1 (control and cases No. 10 to No. 12) or Formulation XXI (cases No. 13 and No. 14) containing 150 mg of the dry powder of earthworms W-9 or W-19, respectively, over a period of 21 to 29 days. The main symptoms of these cases were as follows.

Case No. 10 (male, age 54): thrombosis, hypertension
Case No. 11 (male, age 45): deep-vein thrombosis
Case No. 12 (female, age 40): ditto
Case No. 13 (female, age 34): hypertension
Case No. 14 (male, age 46): deep-vein thrombosis Each of these patients and the control was monitored during the administration period for the values of aPTT, Fibgn, FDP, tPA and plasminogen activator inhibitor-1, referred to as PAI-1 hereinbelow, to give the results shown in Table 8 below.

TABLE 8

| Case No. | Days of administration | aPTT, seconds | Fibgn, mg/dl | FDP, ng/ml | tPA, ng/ml | PAI-1, ng/ml |
|---|---|---|---|---|---|---|
| Control | 0 | 32 | 231 | 58 | 11.6 | 2.6 |
| | 1 | 32 | 231 | 50 | 11.4 | 3.3 |
| | 2 | 29 | 237 | 162 | 13.4 | 2.2 |
| | 3 | 31 | 260 | 59 | 11.4 | 2.2 |
| | 4 | 27 | 301 | 66 | 13.2 | 2.7 |
| | 15 | 30 | 249 | 66 | 10.8 | 2.9 |
| | 29 | 29 | 261 | 66 | 11.2 | 4.5 |
| 10 | 0 | 30 | 229 | 230 | 13.4 | 4.8 |
| | 1 | 31 | 229 | 170 | 14.8 | 4.9 |
| | 2 | 30 | 195 | 110 | 11.6 | 2.1 |
| | 3 | 28 | 216 | 125 | 12.2 | 4.8 |
| | 4 | 28 | 215 | 102 | 11.2 | 4.2 |
| | 21 | 29 | 220 | 68 | 10.8 | 3.1 |
| 11 | 0 | 28 | 278 | 190 | 12.6 | 10.7 |
| | 1 | 28 | 270 | 260 | 13.8 | 8.5 |
| | 2 | 28 | 200 | 180 | 13.4 | 10.3 |
| | 3 | 24 | 222 | 190 | 11.4 | 7.3 |
| | 4 | 28 | 228 | 96 | 17.2 | 7.8 |
| | 11 | 28 | 234 | 105 | 15.6 | 4.7 |
| | 24 | 30 | 239 | 65 | 13.0 | 4.9 |
| 12 | 0 | 30 | 260 | 185 | 12.6 | 7.4 |
| | 1 | 31 | 225 | 260 | 10.4 | 7.4 |
| | 4 | 32 | 210 | 204 | 10.8 | 7.3 |
| | 7 | 32 | 255 | 182 | 11.4 | 5.7 |
| | 15 | 30 | 277 | 152 | 8.2 | 5.2 |
| | 25 | 31 | 250 | 140 | 10.2 | 4.7 |
| 13 | 0 | 26 | 340 | 54 | 9.8 | 2.9 |
| | 1 | 32 | 240 | 60 | 10.2 | 3.2 |
| | 2 | 28 | 188 | 78 | 11.4 | 2.8 |
| | 4 | 34 | 234 | 210 | 13.6 | 2.7 |
| | 13 | 32 | 300 | 136 | 10.4 | 2.2 |
| | 21 | 30 | 296 | 62 | 10.2 | 1.7 |
| 14 | 0 | 29 | 255 | 200 | 12.6 | 4.9 |
| | 1 | 29 | 250 | 185 | 10.6 | 4.1 |
| | 2 | 30 | 222 | 180 | 11.2 | 3.1 |
| | 3 | 30 | 246 | 240 | 17.8 | 3.0 |
| | 4 | 32 | 250 | 210 | 17.4 | 4.4 |
| | 11 | 28 | 225 | 190 | 16.2 | 5.5 |
| | 18 | 29 | 235 | 155 | 14.4 | 4.0 |
| | 25 | 32 | 240 | 65 | 13.8 | 3.9 |

As is understood from these results, the administration of the dry powder of earthworms had almost no effect of shortening the aPTT or decomposition of Fibgn to be free from the side effects unavoidably caused by the administration of a conventional thrombolytic enzymatic medicament.

In the case No. 10 suffering complication of thrombosis and hypertension, whose maximum and minimum blood pressures were 155 and 95 mmHg, respectively, the value of FDP in the plasma was as high as about 4 times of the value in the healthy person at the start of the test indicating that his blood contained a large amount of fibrin. When he was administrated with the dry powder of earthworms, an active thrombolytic effect was exhibited by the administration of 1 to 2 days and the values of FDP, tPA and PAI-1 were at the respective normal levels of healthy persons to indicate complete cure of the thrombosis along with the decrease of the blood pressure to the normal maximum and minimum values of 135 and 85 mmHg, respectively.

In the case No. 13 suffering hypertension, whose maximum and minimum blood pressures were 145 and 105 mmHg, respectively, the value of FDP was increased to about 4 times of the initial value and the value of tPA was also remarkably increased by the administration of 4 days. The tendency of increase in the FDP continued until the 13th days of administration but the values of FDP, tPA and PAI-1 were decreased at the 21st days of the administration and thereafter to level off at the respective normal values as in healthy persons indicating dissolution of the fibrin lumps along with a decrease in the blood pressure to normal maximum and minimum values of 130 and 83 mmHg, respectively.

In each of the cases No. 11, No. 12 and No. 14 suffering deep-vein thrombosis, the value of FDP in the plasma was remarkably increased on the 12th day of administration although the value was as high as 3 to 3.5 times of that of healthy persons at the start of the test. The thus increased value of FDP was maintained for a while and then decreased. In the cases No. 11 and No. 14, the values of FDP, tPA and PAI-1 were decreased to the respective same levels as in healthy persons after 24 to 25 days of administration indicating dissolution and disappearance of fibrin lumps. In the case No. 12, each of the values of FDP, tPA and PAI-1 was decreased on the 25th day of administration indicating remarkable improvement in the condition of deep-vein thrombosis though without complete cure.

The above described results of the oral administration test of the dry powder of earthworms alone clearly support the conclusion that the medicament is effective to completely cure or remarkably improve the condition of thrombosis or deep-vein thrombosis or a complication thereof with hypertension and/or lipemia. The hypertension or lipemia as a counterpart of the complication can also be cured completely along with the thrombosis. Further, it is also clear that the thrombi in the patient of hypertension or complication of hypertension or hypotonia and lipemia can be dissolved by the administration of the dry powder of earthworms leading to complete cure of the hypertension, hypotonia and lipemia.

In addition, combined administration of the dry powder of earthworms and a conventional anticoagulant Warfarin Potassium was effective to completely cure or remarkably improve the condition of deep-vein thrombosis or complication thereof with lipemia.

In the above described administration test, the various analytical values were obtained each in the following manner. Thus, the value of FDP in ng/ml in the plasma was determined by using a FDP (D-Dimer) ELISA (Enzyme-linked immunosorbent assay) kit (Asserachrom D-Di) sold by Stago Co., France. The value of tPA in ng/ml in the plasma was determined by using a tPA IRMA (immunoradiometric assay) kit (rabbit antihuman tPA) sold by Scripps Clinic Laboratories, U.S.A. The value of PAI-1 in ng/ml in the plasma was determined by using a PAI-1 ELISA kit (goat antihuman PAI-1) sold by Biopool Co., Sweden. The values of aPTT in seconds, Fibgn in ng/dl, TC in mg/dl and TG in mg/dl were determined each in a conventional method or by using a conventional kit.

What is claimed is:

1. A method for controlling thrombosis in a mammal in need thereof which comprises orally administering an effective amount of earthworm powder to said mammal which has been prepared by the steps of:
   a) cleaning living earthworms of dirt on the body surface and fecal mud in the digestive tract by placing the living earthworms in an acidic aqueous solution having a pH of from 3 to 6.5 for from 0.1 to 5 hours;
   b) pulverizing the living earthworms into a paste;
   c) freezing the paste at a temperature of $-10°$ C. to $-60°$ C. followed by freeze-drying the paste at said temperature for 5 to 12 hours under a vacuum of 0.01 to 0.2 mm Hg;
   d) vacuum-drying the paste in a step-wise progression of 5 to 15 hours at 20° C. to 30° C. under 0.01 to 0.2 mm Hg, 10 to 20 hours at 35° C. to 50° C. under 0.1 to 0.5 mm Hg; and 0.1 to 19 hours at 70° C. to 80° C. under 0.001 to 5 mm Hg.

2. A method as in claim 1 wherein the amount of powder administered is from about 0.001 g to 15 g per day.

3. A method as in claim 1 wherein the amount of powder administered is from about 0.002 g to 9 g per day.

* * * * *